(12) United States Patent
Iwahori et al.

(10) Patent No.: US 8,806,691 B2
(45) Date of Patent: Aug. 19, 2014

(54) ELECTRIC TOOTHBRUSH

(71) Applicant: Omron Healthcare Co., Ltd., Kyoto (JP)

(72) Inventors: Toshiyuki Iwahori, Kyoto (JP); Akitoshi Miki, Ibaraki (JP); Jun Shimoyama, Kyoto (JP); Takashi Torihama, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/836,394

(22) Filed: Mar. 15, 2013

(65) Prior Publication Data

US 2013/0198980 A1    Aug. 8, 2013

Related U.S. Application Data

(63) Continuation of application No. 12/922,303, filed as application No. PCT/JP2009/052702 on Feb. 17, 2009, now abandoned.

(30) Foreign Application Priority Data

Mar. 13, 2008    (JP) ................... 2008-064628

(51) Int. Cl.
*A61C 17/34*    (2006.01)
*A61C 17/16*    (2006.01)

(52) U.S. Cl.
USPC .............. 15/22.1; 433/118; 433/122; 310/81; 74/87

(58) Field of Classification Search
USPC .......... 15/22.1, 22.2; 433/122, 103, 107, 118, 433/80, 216; 310/15, 25, 36, 81; 601/46, 601/67, 69, 70, 84, 89, 92, 93, 107, 108, 601/112, 114, 81; 74/87
See application file for complete search history.

(56) References Cited

U.S. PATENT DOCUMENTS 1,803,458 A    5/1931    Berry
3,685,080 A    8/1972    Hubner
(Continued)

FOREIGN PATENT DOCUMENTS

DE    196 54 319 C1    8/1998
JP    U-7-24127    5/1995
(Continued)

OTHER PUBLICATIONS

JP2004008974A (machine translation), 2004.*

(Continued)

*Primary Examiner* — Mark Spisich
*Assistant Examiner* — Andrew A Horton
(74) *Attorney, Agent, or Firm* — Oliff PLC

(57) ABSTRACT

The invention provides an electric toothbrush capable of changing a resonant frequency and vibration amplitude of an eccentric shaft. An electric toothbrush of the present invention includes a motor, an eccentric shaft with one end fixed to a rotation shaft of the motor, and a stem serving as a vibration transmitting component having a bearing for supporting the other end of the eccentric shaft for transmitting vibration generated in accordance with rotation of the eccentric shaft to a brush portion. In the electric toothbrush, the eccentric shaft is formed so that a gravity center position is movable at least in one direction among a direction in which a distance to a shaft center is changed and an axial direction.

3 Claims, 19 Drawing Sheets

(56) References Cited

U.S. PATENT DOCUMENTS

| | | |
|---|---|---|
| 4,591,748 A | 5/1986 | Greer |
| 4,940,336 A | 7/1990 | Dryga et al. |
| 5,651,157 A | 7/1997 | Hahn |
| 5,987,681 A | 11/1999 | Hahn et al. |
| 6,766,548 B1 * | 7/2004 | Lukas et al. ............ 15/22.1 |

FOREIGN PATENT DOCUMENTS

| | | | | |
|---|---|---|---|---|
| JP | A-10-192054 | | 7/1998 | |
| JP | 2004008974 A | * | 1/2004 | ............ B06B 1/04 |
| RU | 2 296 534 C2 | | 4/2007 | |
| WO | WO 03096860 A1 | * | 11/2003 | ............ A46B 13/02 |
| WO | WO 2008/026383 A1 | | 3/2008 | |

OTHER PUBLICATIONS

International Search Report for International Patent Application No. PCT/JP2009/052702, mailed on Jun. 2, 2009 (w/ English translation).

Office Action issued in Russian Application No. 2010141820 dated Nov. 3, 2011 (with trans).

Aug. 28, 2012 Office Action issued in U.S. Appl. No. 12/922,303.

Dec. 19, 2012 Office Action issued in U.S. Appl. No. 12/922,303.

* cited by examiner (a)   (b)

(a)  (b)

(a)  (b)

(a)　　　　　　(b)

(a)　　　(b)　　　(c)

ELECTRIC TOOTHBRUSH

CROSS REFERENCE

This is a Continuation of application Ser. No. 12/922,303 filed Oct. 1, 2010, now abandoned, which in turn is a Continuation of International Application No. PCT/JP2009/052702 filed Feb. 17, 2009 claiming the convention priority of Japanese Patent Application No. 2008-064628 filed Mar. 13, 2008. The disclosure of the prior application[s] is hereby incorporated by reference herein in its entirety.

TECHNICAL FIELD

The present invention relates to an electric toothbrush.

BACKGROUND ART

Conventionally, there is an electric toothbrush for generating vibration by rotating an eccentric shaft with a motor (refer to Patent Document 1). In such an electric toothbrush, a gravity center position of the eccentric shaft (a distance from a gravity center to a shaft center and a position in an axial direction of the eccentric shaft) is not changed. Therefore, neither resonant frequency nor vibration amplitude is changed.

However, there are cases where the resonant frequency and the vibration amplitude of the eccentric shaft are appropriately changeable for various reasons of obtaining feel of brushing at the time of brushing teeth, a brushing effect in accordance with a part of the teeth to be brushed, and the like.

Patent Document 1: Japanese Unexamined Patent Publication No. H 10-192054

DISCLOSURE OF THE INVENTION

Problems to be Solved by the Invention

An object of the present invention is to provide an electric toothbrush capable of changing a resonant frequency and vibration amplitude of an eccentric shaft.

Means for Solving the Problems

In the present invention, the following means are adopted in order to solve the above problems.

That is, an electric toothbrush of the present invention includes:
a motor,
an eccentric shaft with one end fixed to a rotation shaft of the motor, and
a vibration transmitting component for transmitting vibration generated in accordance with rotation of the eccentric shaft to a brush portion, wherein
the eccentric shaft is formed so that a gravity center position is movable at least in one direction among a direction in which a distance to a shaft center is changed and an axial direction.

According to the present invention, when the gravity center position of the eccentric shaft is moved in the direction in which the distance to the shaft center is changed, vibration amplitude of the eccentric shaft can be changed. When the gravity center position of the eccentric shaft is moved in the axial direction, a resonant frequency of the eccentric shaft can be changed.

The eccentric shaft may include a plurality of weights positioned so that gravity centers are shifted from the shaft center, and at least one of the plurality of weights may be provided rotatably relative to an eccentric shaft main body.

Thereby, when the rotatable weight is rotated, a positional relationship of the gravity centers of the weights in the rotation direction relative to the shaft center is changed. Therefore, a distance between the gravity center position of the entire eccentric shaft and the shaft center can be changed.

The electric toothbrush may include a first weight fixed to the eccentric shaft main body and positioned so that a gravity center is shifted from the shaft center, and
a second weight positioned so that a gravity center is shifted from the shaft center with a rotation range regulated so that rotation relative to the eccentric shaft main body is permitted within a fixed range, wherein
a regulated position of the second weight in a rotation direction may be differentiated by a rotation direction of the eccentric shaft.

Thereby, the distance between the gravity center position of the eccentric shaft and the shaft center can be changed by the rotation direction of the eccentric shaft.

The eccentric shaft may include a weight positioned so that a gravity center is shifted from the shaft center, and the weight may be provided movably in the axial direction relative to an eccentric shaft main body.

Thereby, the gravity center position of the eccentric shaft can be moved in the axial direction.

A male screw may be formed in the eccentric shaft main body, and
a female screw to be screwed onto the male screw may be formed in the weight.

Thereby, the weight can be moved in the axial direction by the rotation of the eccentric shaft main body. The moving direction of the weight can be changed by the rotation direction of the eccentric shaft main body.

The weight may be fitted to the eccentric shaft main body slidably in the axial direction.

Thereby, the weight is moved by gravitational force in accordance with a posture of the electric toothbrush. Thus, the gravity center position of the eccentric shaft can be moved in the axial direction.

The eccentric shaft may include:
a first weight fixed to the eccentric shaft main body and positioned so that a gravity center is shifted from the shaft center, and
a second weight positioned so that a gravity center is shifted from the shaft center, the second weight being adapted to be rotatable relative to the eccentric shaft main body, and
the first weight and the second weight may be arranged in line in the axial direction so that a plurality of teeth provided in an end surface of the first weight and a plurality of teeth provided in an end surface of the second weight are meshed with each other, thereby forming a ratchet mechanism.

Thereby, in a case where the eccentric shaft main body is rotated in a certain direction, a relative positional relationship between the first weight and the second weight is not changed. When the eccentric shaft main body is rotated in the opposite direction, the second weight is rotated relative to the first weight. Therefore, in this case, the distance between the gravity center position of the eccentric shaft and the shaft center can be changed. In a case where the second weight is rotated relative to the first weight, the second weight is also moved in the axial direction for getting over the teeth respectively provided in the weights. Thus, the gravity center position of the eccentric shaft can be periodically moved in the axial direction.

The eccentric shaft may include:
an eccentric shaft main body, a weight positioned so that a gravity center is shifted from the shaft center, and a coil spring with one end fixed to the eccentric shaft main body and the other end fixed to the weight.

Thereby, the weight is moved by the gravitational force and extension and compression of the coil spring in accordance with the posture of the electric toothbrush. Thus, the gravity center position of the eccentric shaft can be moved in the axial direction. The eccentric shaft main body and the weight are connected via the coil spring. Thus, at the time of start-up, the weight is rotated after the rotation of the eccentric shaft main body. Therefore, at the time of start-up, the vibration amplitude of the eccentric shaft can be gradually increased.

The eccentric shaft may include an eccentric shaft main body, and a weight positioned so that a gravity center is shifted from the shaft center, and the eccentric shaft main body and the weight may be arranged in line in the axial direction while a fluid (fluid for transmitting rotation power (such as oil and grease)) is placed between the eccentric shaft main body and the weight.

Thereby, by the so-called principle of a fluid clutch, the weight is slowly rotated at the beginning, rotation speed is gradually increased, and the rotation speed becomes the same as rotation speed of the eccentric shaft main body in the end. Accordingly, the gravity center of the eccentric shaft is gradually moved from a position of the shaft center to a position distant from the shaft center. Therefore, at the time of start-up, the vibration amplitude of the eccentric shaft is gradually increased.

A bearing for supporting the other end of the eccentric shaft may be provided in the vibration transmitting component.

When such a configuration is adopted, the vibration generated in the vicinity of the bearing which is provided in the vibration transmitting component can be transmitted to the brush portion. The bearing is provided on the side of the other end of the eccentric shaft, that is, in the vicinity of the brush portion which is distant from the rotation shaft of the motor. Thus, the vibration can be efficiently transmitted to the brush portion.

The above configurations can be adopted in combination as far as possible.

Effect of the Invention

As described above, according to the present invention, the resonant frequency and the vibration amplitude of the eccentric shaft can be changed.

DESCRIPTION OF SYMBOLS

Figure 1:
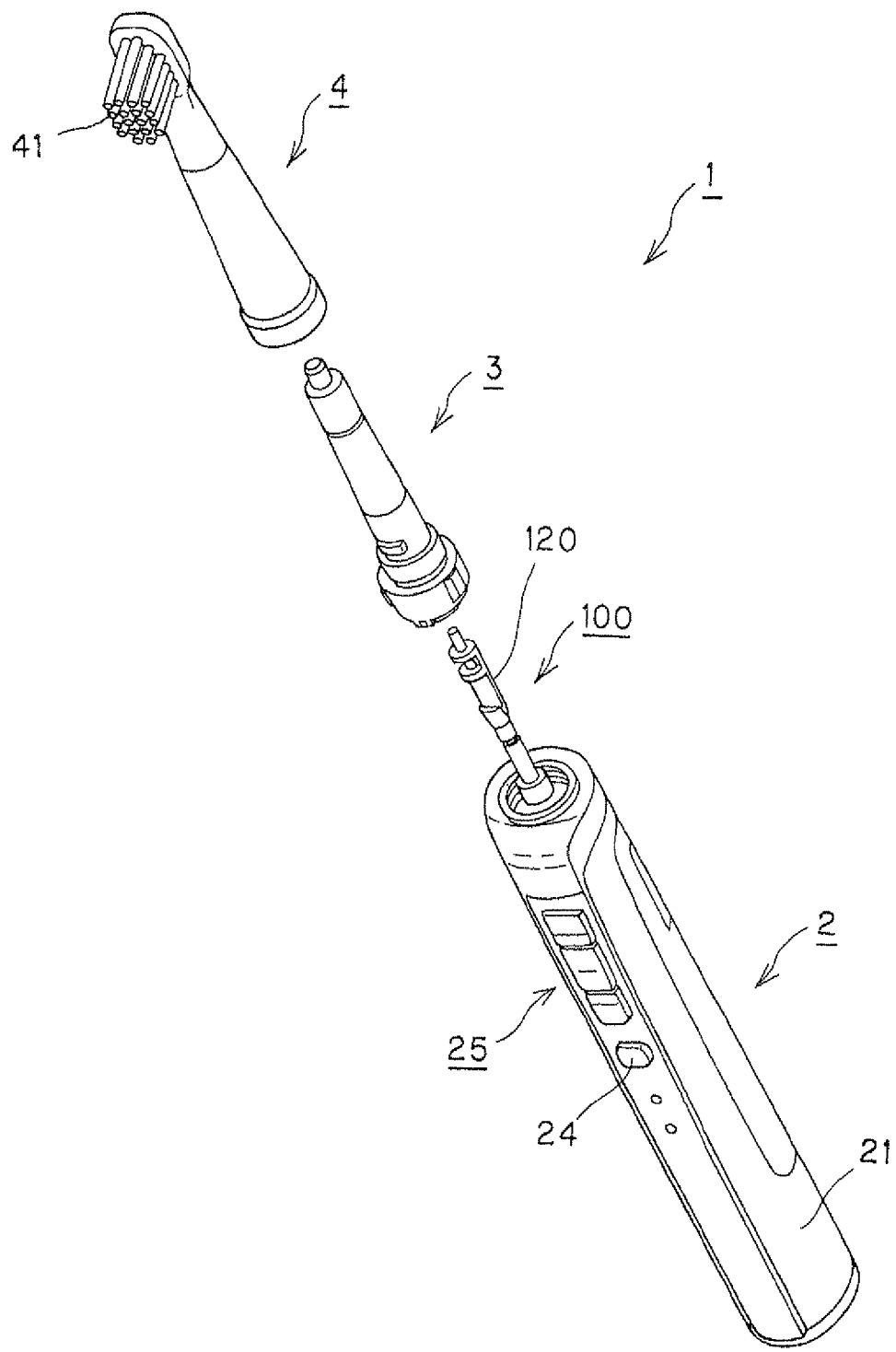
FIG. 1 is an exploded perspective view of parts of an electric toothbrush according to an embodiment of the present invention.

1 Electric toothbrush
2 Electric toothbrush main body
21 Case
22 Battery
23 Motor
23a Rotation shaft
24 Switch
25 Operation unit
3 Stem
31 Bearing
32 Inner wall surface
4 Brush component
41 Brush portion
100 Eccentric shaft
110 Eccentric shaft main body
111, 112, 113, 114, 115, 116, 117 Eccentric shaft main body
111a, 112a, 113a, 114a, 115a, 116a, 117a Hole portion 112b Shaft portion
112c Male screw
112d First position regulation portion
112e Second position regulation portion
113b Insertion hole
114b Protruding portion
114c First weight
115b First weight
115c Tooth
117X Trunk
117Y Metal component
117Ya Concave portion
120 Weight
121 First weight
122 Second weight
123 Weight
124 First weight
124a Weight main body portion
124b Cutout portion
124c Substantially-disc portion
125 Second weight
125a Weight main body portion
125b Shaft portion
125c Lock projection
125d Disc portion
126 Weight
126a Pass-through hole
127 Weight
127a Shaft portion
127b Shaft portion
128 Second weight
128a Shaft portion
128b Slit portion
129 Second weight
129a Shaft portion
129b Weight main body portion
129c Tooth
130 Weight
130a Shaft portion
131 Weight
131a Shaft portion
131b Convex portion

BEST MODE FOR CARRYING OUT THE INVENTION

With reference to the drawings, the best mode for carrying out the invention will be exemplified and described in detail based on an embodiment and examples. However, the scope of the invention is not limited to only size, materials, shapes, and relative arrangement of constituent components described in the examples unless particularly specifically described.

(Embodiment)

Figure 2:
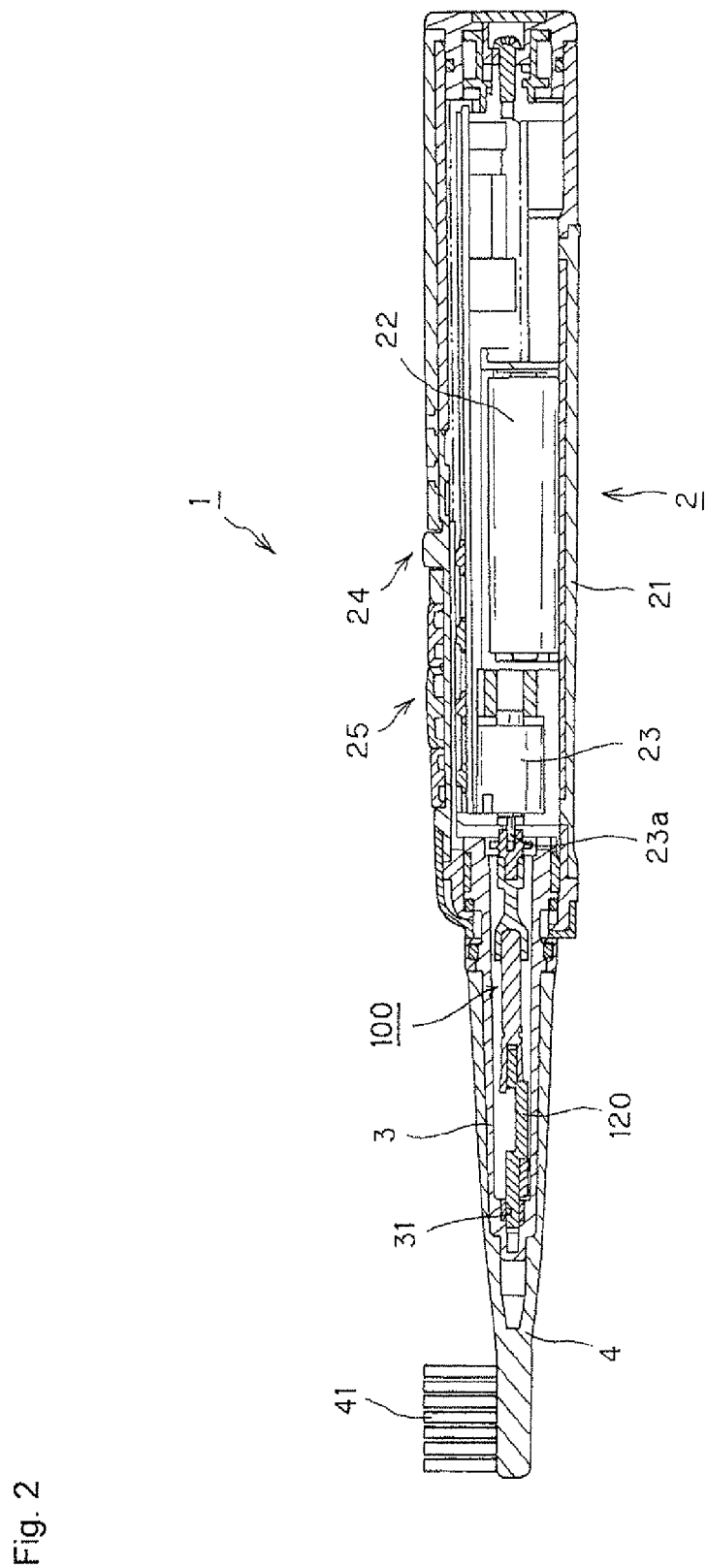
FIG. 2 is a schematic sectional view of the electric toothbrush according to the embodiment of the present invention.
Figure 3:
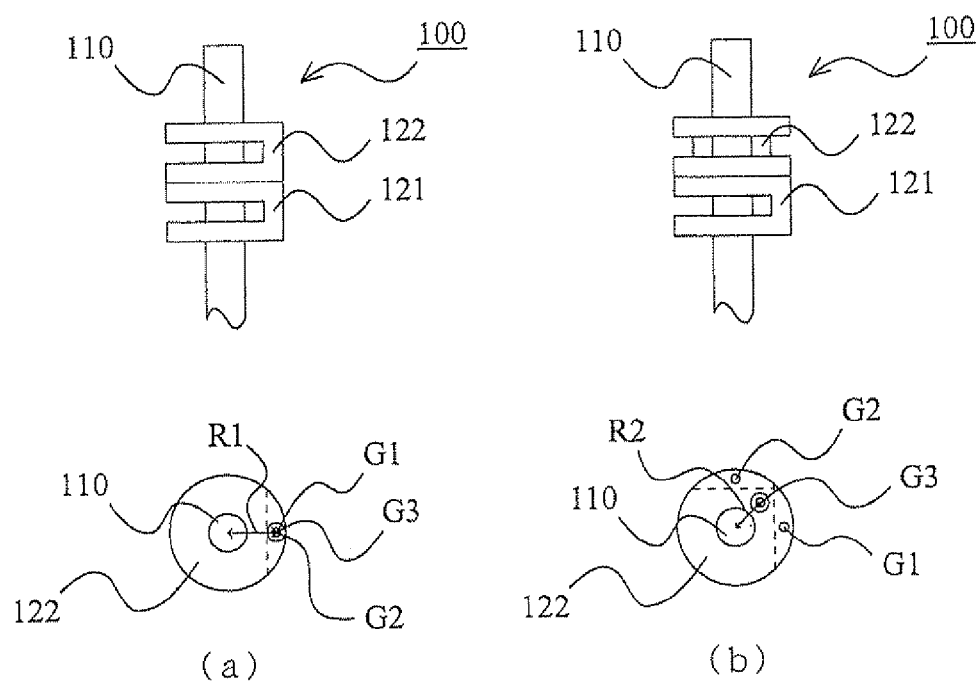
FIGS. 3(a) and 3(b) are illustrative views for a mechanism in a case where a distance between a gravity center position of an eccentric shaft and a shaft center is changed in the electric toothbrush according to the embodiment of the present invention.
Figure 4:
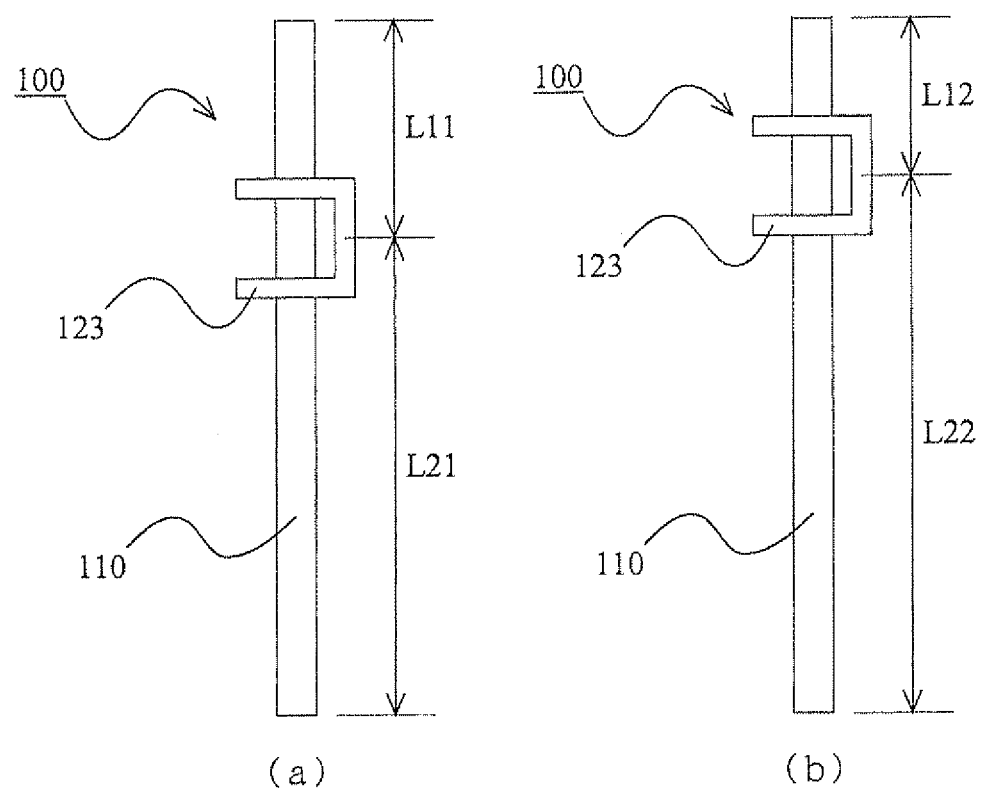
FIGS. 4(a) and 4(b) are illustrative views for a mechanism in a case where the gravity center position of the eccentric shaft is moved in the axial direction in the electric toothbrush according to the embodiment of the present invention.

With reference to FIGS. 1 to 4(b), an electric toothbrush according to the embodiment of the present invention will be described. FIG. 1 is an exploded perspective view of parts of the electric toothbrush according to the embodiment of the present invention. FIG. 2 is a schematic sectional view of the electric toothbrush according to the embodiment of the present invention. FIGS. 3(a) and 3(b) are illustrative views for a mechanism in a case where a distance between a gravity center position of an eccentric shaft and a shaft center is changed in the electric toothbrush according to the embodiment of the present invention. FIGS. 4(a) and 4(b) are illustrative views for a mechanism in a case where the gravity center position of the eccentric shaft is moved in the axial direction in the electric toothbrush according to the embodiment of the present invention.

(Electric Toothbrush)

With reference to FIGS. 1 and 2, the entire configuration and the like of the electric toothbrush according to the embodiment of the present invention will be described. An electric toothbrush 1 is provided with an electric toothbrush main body 2, an eccentric shaft 100, a stem 3 serving as a vibration transmitting component, and a brush component 4 having a brush portion 41.

The electric toothbrush main body 2 is provided with a case 21, a battery 22 and a motor 23 accommodated inside the case 21, a switch 24 for turning ON/OFF a power supply, and an operation unit 25 including a group of buttons for changing various modes. One end of the eccentric shaft 100 is fixed to a rotation shaft 23a of the motor 23. The eccentric shaft 100 is formed so as to protrude from an opening of a front end of the case 21 toward the outside of the case 21. A weight 120 positioned so that a gravity center is shifted from the shaft center is provided in the eccentric shaft 100. The other end of the eccentric shaft 100 is supported by a bearing 31 provided in the stem 3.

The brush component 4 is installed so as to cover the stem 3. A main body part of the brush component 4 is formed by a tubular member so as to be installed to the stem 3, and the brush portion 41 is provided in a front end thereof. The brush component 4 is a consumable item and hence detachable from the stem 3 so as to be timely replaced by a new item.

(Description of Operation of Electric Toothbrush)

An operation of the electric toothbrush 1 configured as above will be described. When the power supply is turned on by the switch 24, the rotation shaft 23a of the motor 23 is rotated, and the eccentric shaft 100 fixed to the rotation shaft 23a is rotated. As described above, the weight 120 positioned so that the gravity center is shifted from the shaft center is provided in the eccentric shaft 100. Therefore, when the eccentric shaft 100 is rotated in a state that a distal end of the eccentric shaft 100 is not supported by the bearing 31, the eccentric shaft 100 itself is rotated while performing a motion as if swirling around the shaft center. Thereby, when the eccentric shaft 100 is rotated in a state that the eccentric shaft 100 is supported by the bearing 31, an outer wall surface of the eccentric shaft 100 in the vicinity of the distal end can be repeatedly collided with an inner wall surface of the bearing 31a number of times in a short period of time.

By performing such an operation, the stem 3 provided with the bearing 31 can be vibrated via the bearing 31. By vibrating the stem 3, the vibration can be transmitted to the brush component 4 fixed to the stem 3. Therefore, the brush portion 41 is vibrated by the vibration of the brush component 4. Thus, when the brush portion 41 is applied onto teeth, the teeth can be brushed.

(Eccentric Shaft)

Particularly, with reference to FIGS. 3(a), 3(b), 4(a), and 4(b), the eccentric shaft in the electric toothbrush according to the embodiment of the present invention will be described in detail. The eccentric shaft 100 in the present embodiment is formed so that a gravity center position is movable at least in one direction among the direction in which a distance to a shaft center is changed and the axial direction.

Firstly, with reference to FIGS. 3(a) and 3(b), a basic configuration and a mechanism in a case where the gravity center position of the eccentric shaft 100 is moved in the direction in which the distance to the shaft center is changed will be described. In this case, two weights (hereinafter, referred to as the first weight 121, the second weight 122) are provided in the eccentric shaft main body 110. The first weight 121 and the second weight 122 are provided at positions where gravity centers are shifted from the shaft center (in the figures, the symbol G1 denotes a gravity center position of the first weight 121 and the symbol G2 denotes a gravity center position of the second weight 122). Shapes and weights of the first weight 121 and the second weight 122 are the same.

The second weight 122 is rotatable relative to the eccentric shaft main body 110. FIG. 3(a) shows a case where the gravity center position G1 of the first weight 121 and the gravity center position G2 of the second weight 122 correspond to each other seen in the axial direction. In this case, when a weight of the eccentric shaft main body 110 is ignored, a gravity center position G3 of the eccentric shaft 100 seen in the axial direction corresponds to G1 and G2. The symbol R1 denotes a distance between the gravity center position G3 of the eccentric shaft 100 and the shaft center at this time.

FIG. 3(b) shows a case where the second weight 122 is rotated by 90° from the state shown in FIG. 3(a). In this case, the gravity center position G1 of the first weight 121 and the gravity center position G2 of the second weight 122 are in a positional relationship in which the gravity center positions are shifted from each other by 90° relative to the shaft center seen in the axial direction. When the weight of the eccentric shaft main body 110 is ignored, the gravity center position G3 of the eccentric shaft 100 seen in the axial direction is a position of a midpoint between G1 and G2. When the symbol R2 denotes a distance between the gravity center position G3 of the eccentric shaft 100 and the shaft center at this time, R2<R1.

As described above, by rotating the second weight 122, the gravity center position of the eccentric shaft 100 can be moved in the direction in which the distance to the shaft center is changed.

In the above description, the weight of the eccentric shaft main body 110 is ignored for convenience sake. However, as a matter of course, the actual gravity center of the eccentric shaft 100 is also influenced by the weight of the eccentric shaft main body 110. However, needless to say, the fact remains that by rotating the second weight 122, the distance between the gravity center of the eccentric shaft 100 and the shaft center is changed. For convenience sake of description, the case where the shapes and the weights of the first weight 121 and the second weight 122 are the same is exemplified and described in order to simplify the model. However, even when these shapes and weights are differentiated, needless to say, the distance between the gravity center of the eccentric shaft 100 and the shaft center is changed. Even when three or more weights are provided, needless to say, by rotating at least one of the weights, the distance between the gravity center of the eccentric shaft 100 and the shaft center is changed.

Next, with reference to FIGS. 4(a) and 4(b), a basic configuration and a mechanism in a case where the gravity center position of the eccentric shaft 100 is moved in the axial direction will be described. In this case, a weight 123 is provided movably in the axial direction relative to the eccentric shaft main body 110. Thereby, a distance in the axial direction between the bearing and a gravity center position of the weight 123 (denoted by the symbol L11 in FIG. 4(a) and the symbol L12 in FIG. 4(b)) and a distance in the axial direction between a part fixed to the rotation shaft of the motor and the gravity center position of the weight 123 (denoted by the symbol L21 in FIG. 4(a) and the symbol L22 in FIG. 4(b)) can be changed. In FIGS. 4(a) and 4(b), FIG. 4(b) shows an example in which a position of the weight 123 is moved closer to the side of the bearing than an example shown in FIG. 4(a). At this time, L11>L12, and L21<L22.

As described above, by moving the weight 123 in the axial direction, the gravity center position of the eccentric shaft 100 can be moved in the axial direction.

In the above description, the case of one weight is exemplified and described. However, even when two or more weights are provided, needless to say, by moving at least one of the weights in the axial direction, the gravity center position of the eccentric shaft 100 can be moved in the axial direction.

By combining the configuration shown with reference to FIGS. 3(a) and 3(b) and the configuration shown with reference to FIGS. 4(a) and 4(b), needless to say, the gravity center position of the eccentric shaft 100 can be moved in the direction in which the distance to the shaft center is changed, and at the same time, the gravity center position of the eccentric shaft 100 can be moved in the axial direction.

(Advantages of the Present Embodiment)

As described above, with the electric toothbrush 1 according to the present embodiment, the eccentric shaft 100 for vibrating the brush portion 41 is formed so that the gravity center position is movable at least in one direction among the direction in which the distance to the shaft center is changed and the axial direction.

Therefore, by moving the gravity center position of the eccentric shaft 100 in the direction in which the distance to the shaft center is changed, the vibration amplitude of the eccentric shaft 100 can be changed. By moving the gravity center position of the eccentric shaft 100 in the axial direction, the resonant frequency of the eccentric shaft 100 can be changed.

One example of specific advantages obtained by changing the vibration amplitude and the resonant frequency of the eccentric shaft 100 and utilization methods thereof will be described.

In a case where the teeth are brushed by using the electric toothbrush, some users may not obtain actual feel of brushing with a little vibration of the brush portion or stimulation may be too strong for some users with large vibration of the brush portion. Thus, by making the vibration amplitude of the eccentric shaft 100 changeable, the feel of brushing can be changed.

In general, in a case of the electric toothbrush for vibrating the brush portion by the eccentric shaft, the rotation number of the rotation shaft of the motor is set so that resonance is generated in various members including the brush portion in order to efficiently vibrate the brush portion. However, it is generally difficult to reliably generate the resonance due to various errors. Thus, by making the resonant frequency of the eccentric shaft 100 changeable, the resonance can be more reliably generated.

It is confirmed that a vibrating manner of tips of the brush (a degree of sideward vibration and a degree of vertical vibration) is differentiated by the frequency at the time of generating the resonance. When the vibrating manner of the tips of the brush is differentiated, the feel of brushing is also differentiated at the time of brushing the teeth. The vibration manner of the tip which is suitable for brushing is differentiated respectively for a part of the teeth to be brushed. Thus, by making the resonant frequency of the eccentric shaft 100 changeable, the vibrating manner of the tips of the brush can be changed. However, in this case, the resonance is generated with desired resonant frequencies. Thus, there is a need for being able to set a plurality of rotation numbers of the rotation shaft of the motor, or continuously change the rotation number. For example, the mode may be changed by the operation unit 25 so as to change the rotation number to the several other rotation numbers.

Next, several specific examples (the examples) of the eccentric shaft will be described.

FIRST EXAMPLE

Figure 5:
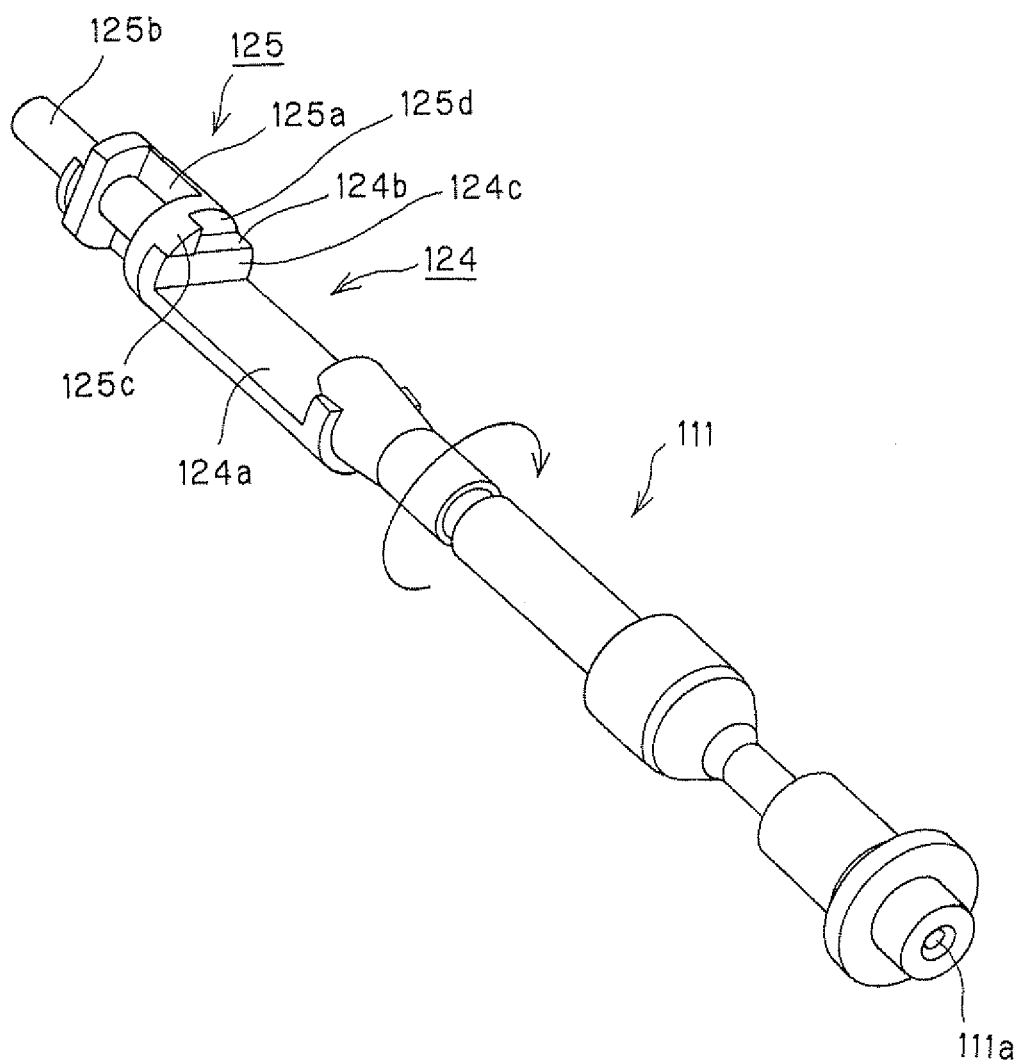
FIG. 5 is a perspective view of the eccentric shaft of the electric toothbrush according to a first example of the present invention.
Figure 6:
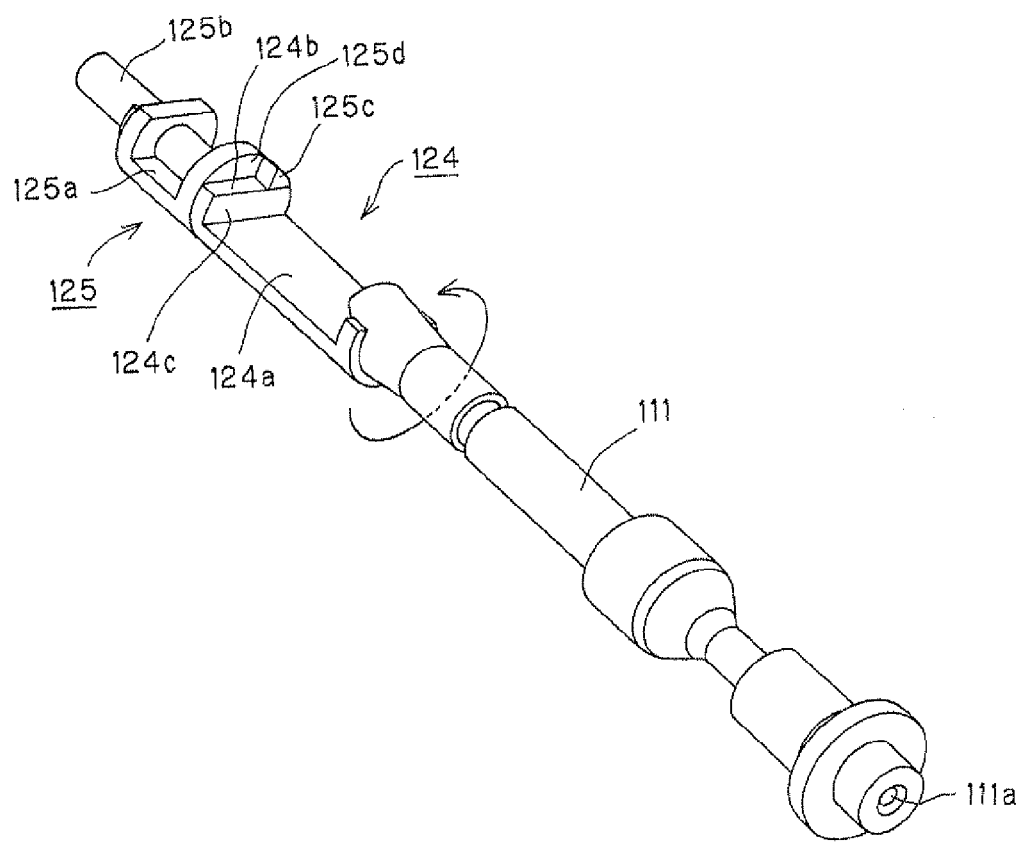
FIG. 6 is a perspective view of the eccentric shaft of the electric toothbrush according to the first example of the present invention.
Figure 7:
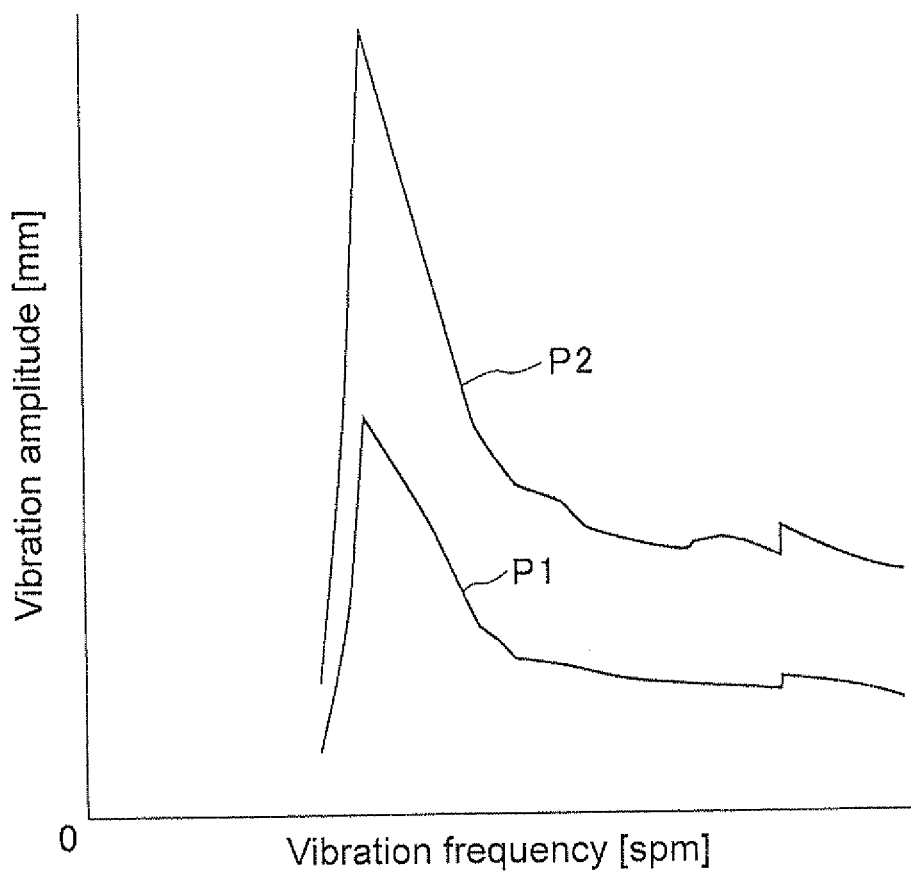
FIG. 7 is a graph showing a relationship between a vibration frequency and vibration amplitude in the electric toothbrush according to the first example of the present invention.

With reference to FIGS. 5 to 7, the electric toothbrush according to a first example of the present invention will be described. The eccentric shaft according to the present example is a more specific example of the embodiment described with reference to FIGS. 3(a) and 3(b). FIGS. 5 and 6 are perspective views of the eccentric shaft of the electric toothbrush according to the first example of the present invention. FIG. 7 is a graph showing a relationship between a vibration frequency and the vibration amplitude in the electric toothbrush according to the first example of the present invention.

In the eccentric shaft according to the present example, a hole portion 111a into which a front end of the rotation shaft 23a of the motor 23 is fitted is provided in one end of the eccentric shaft main body 111. A first weight 124 is fixed to the other end of the eccentric shaft main body 111. In this first weight 124, a substantially-disc portion 124c provided with a cutout portion 124b is provided in a distal end of a weight main body portion 124a. A second weight 125 is provided in line in the axial direction on the side of a front end of the first weight 124. In the second weight 125, a shaft portion 125b supported by the bearing 31 of the stem 3 is provided in a front end of a weight main body portion 125a. A disc portion 125d having a lock projection 125c is provided in the other end of the weight main body portion 125a.

The second weight 125 and the eccentric shaft main body 111 are not fixed to each other. However, inside the electric toothbrush 1, the second weight 125 and the eccentric shaft main body 111 are formed so that center shafts are not shifted from each other. In a specific configuration for realizing this, a convex portion (or a concave portion) is formed on the shaft center of an end surface of the second weight 125, a concave portion (or a convex portion) is provided on the shaft center of an end surface of the eccentric shaft main body 111 (an end surface of the first weight 124), and the second weight 125 and the eccentric shaft main body 111 are arranged in line in the axial direction so that the convex and concave portions are fitted to each other. Alternatively, the inner wall surface of the stem 3 may function as a bearing for the weight main body portion 124a of the first weight 124 and the weight main body portion 125a of the second weight 125.

With the above configuration, the second weight 125 can be rotated within a range in which the lock projection 125c is not disturbed by the substantially-disc portion 124c relative to the eccentric shaft main body 111.

Therefore, in a case where the eccentric shaft main body 111 is rotated in the arrow direction in FIG. 5, the second weight 125 is rotated together with the eccentric shaft main body 111 in a state that the rotation relative to the eccentric shaft main body 111 is regulated by abutting the lock projection 125c with a left end (in the figure) of the cutout portion 124b in the substantially-disc portion 124c. A positional relationship between the gravity center position of the first weight 124 and the gravity center position of the second weight 125 at this time corresponds to the model shown in FIG. 3(b).

In a case where the eccentric shaft main body 111 is rotated in the arrow direction in FIG. 6, the second weight 125 is rotated together with the eccentric shaft main body 111 in a state that the rotation relative to the eccentric shaft main body 111 is regulated by abutting the lock projection 125c with a right end (in the figure) of the cutout portion 124b in the substantially-disc portion 124c. A positional relationship between the gravity center position of the first weight 124 and the gravity center position of the second weight 125 at this time corresponds to the model shown in FIG. 3(a).

As described above, in a case where the eccentric shaft according to the present example is adopted, by switching the rotation direction of the rotation shaft 23a of the motor 23, the gravity center position of the eccentric shaft can be moved in the direction in which the distance to the shaft center is changed. Thereby, the vibration amplitude of the eccentric shaft can be changed. In a case where this example is adopted, the mode may be changed by the operation unit 25 so as to switch the rotation direction of the rotation shaft 23a of the motor 23.

FIG. 7 shows the relationship between the vibration frequency and the vibration amplitude in a case where the present example is adopted. A graph P1 in FIG. 7 corresponds to a case where the eccentric shaft is rotated in the state shown in FIG. 5, and a graph P2 corresponds to a case where the eccentric shaft is rotated in the state shown in FIG. 6.

SECOND EXAMPLE

Figure 8:
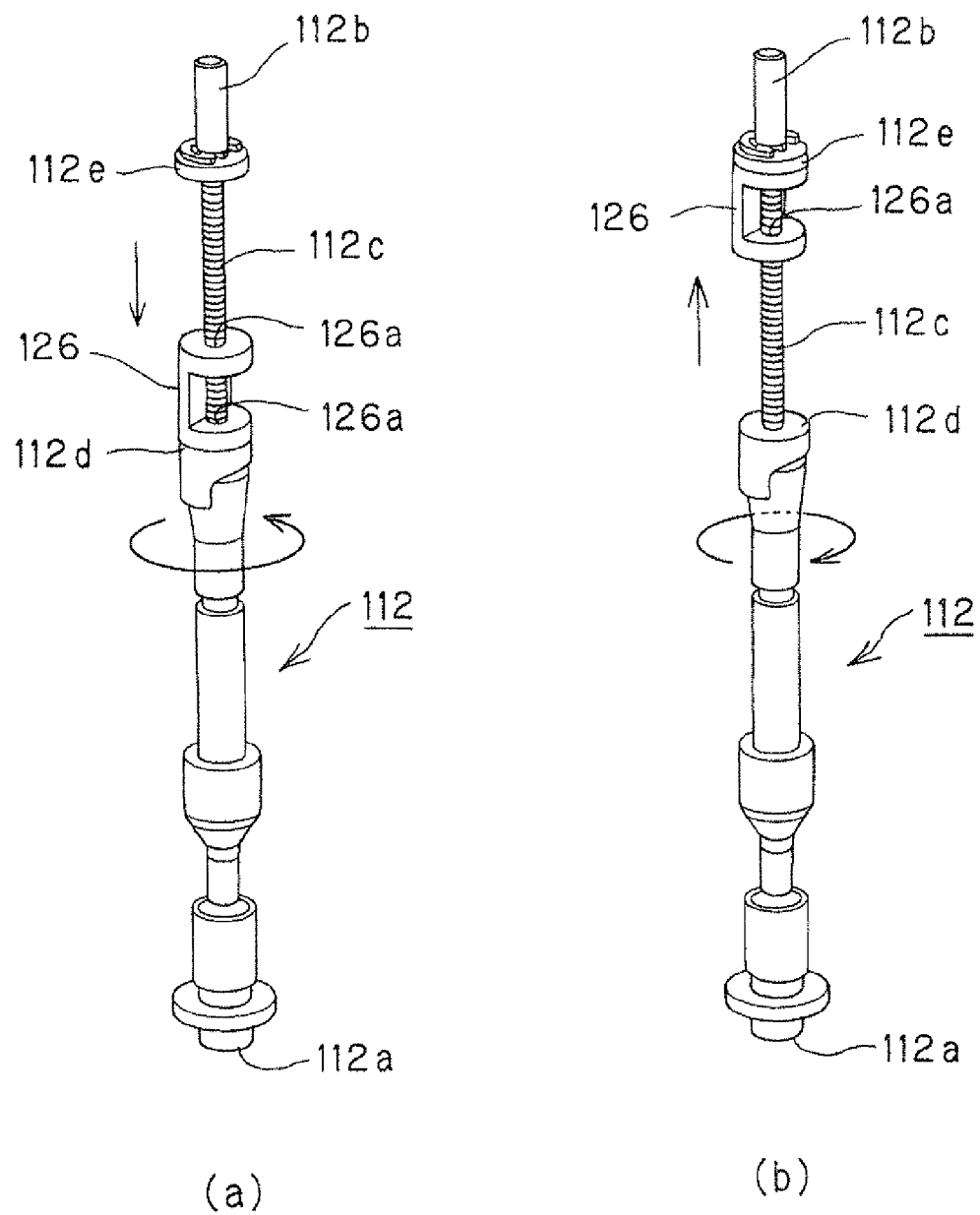
FIGS. 8(a) and 8(b) are perspective views of the eccentric shaft of the electric toothbrush according to a second example of the present invention.
Figure 9:
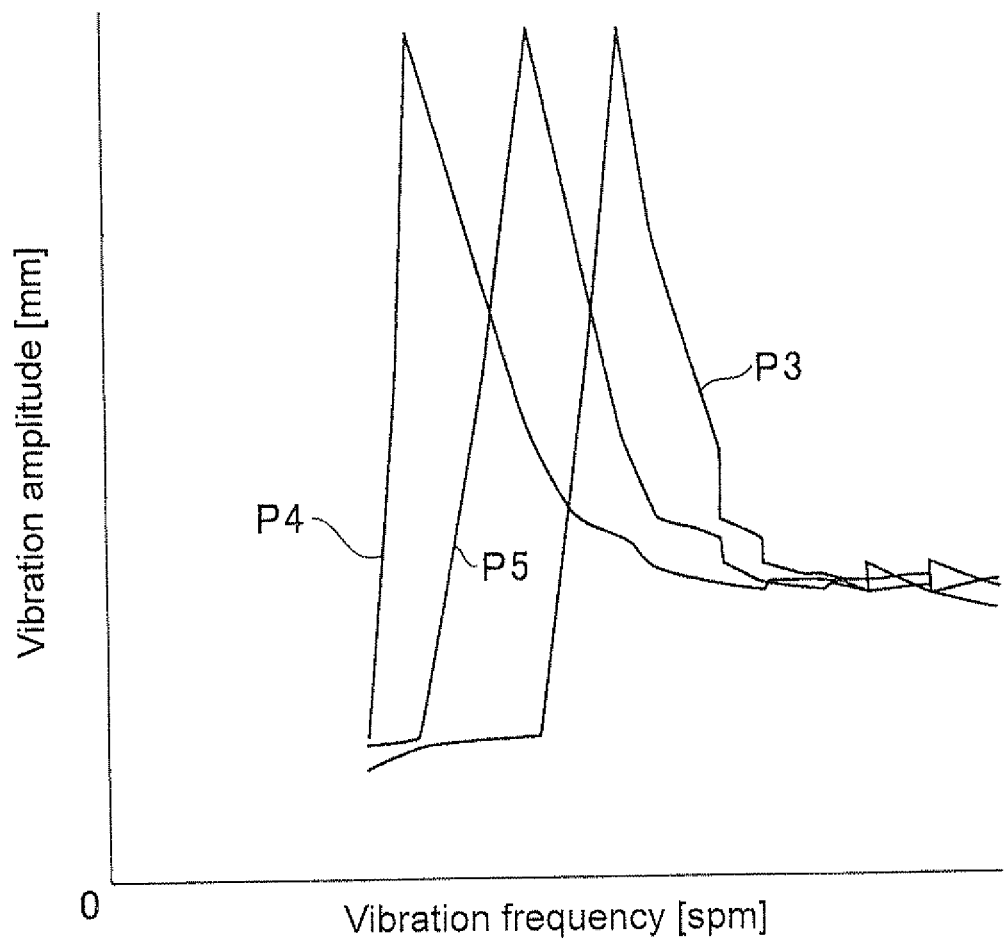
FIG. 9 is a graph showing a relationship between the vibration frequency and the vibration amplitude in the electric toothbrush according to the second example of the present invention.

With reference to FIGS. 8(a), 8(b), and FIG. 9, the electric toothbrush according to a second example of the present invention will be described. The eccentric shaft according to the present example is a more specific example of the embodiment described with reference to FIGS. 4(a) and 4(b). FIGS. 8(a) and 8(b) are perspective views of the eccentric shaft of the electric toothbrush according to the second example of the present invention. FIG. 9 is a graph showing a relationship between the vibration frequency and the vibration amplitude in the electric toothbrush according to the second example of the present invention.

In an eccentric shaft main body 112 in the eccentric shaft according to the present example, a hole portion 112a into which the front end of the rotation shaft 23a of the motor 23 is fitted is provided in one end of the eccentric shaft main body, and a shaft portion 112b supported by the bearing 31 of the stem 3 is provided in the other end. A male screw 112c is formed within a predetermined range of the eccentric shaft main body 112 according to the present example. A first position regulation portion 112d is provided in a lower end in an area in which the male screw 112c is formed, and a disc shape second position regulation portion 112e is provided in an upper end. Pass-through holes 126a in which female screws to be screwed onto the male screw 112c are formed are provided in a weight 126 according to the present example.

With the above configuration, in a case where the eccentric shaft main body 112 is rotated in the arrow direction in FIG. 8(a), the weight 126 is not rotated relative to the eccentric shaft main body 112 or moved downward while being rotated by co-rotation by slower speed than the eccentric shaft main body 112. In a state that the weight 126 is moved to the first position regulation portion 112d, the weight 126 is rotated together with the eccentric shaft main body 112. In a case where the eccentric shaft main body 112 is rotated in the arrow direction in FIG. 8(b), the weight 126 is not rotated relative to the eccentric shaft main body 112 or moved upward while being rotated by the co-rotation by slower speed than the eccentric shaft main body 112. In a state that the weight 126 is moved to the second position regulation portion 112e, the weight 126 is rotated together with the eccentric shaft main body 112. FIG. 8(a) corresponds to the model of FIG. 4(a), and FIG. 8(b) corresponds to the model of FIG. 4(b). In the present example, sufficient clearances are desirably provided between the female screws formed in the pass-through holes 126a and the male screw 112c so that the weight 126 is more reliably moved in the axial direction in a case where the eccentric shaft main body 112 is rotated.

As described above, in a case where the eccentric shaft according to the present example is adopted, by switching the rotation direction of the rotation shaft 23a of the motor 23, the gravity center position of the eccentric shaft can be moved in the axial direction. Thereby, the resonant frequency of the eccentric shaft can be changed. In a case where this example is adopted, the mode may be changed by the operation unit 25 so as to switch the rotation direction of the rotation shaft 23a of the motor 23.

FIG. 9 shows the relationship between the vibration frequency and the vibration amplitude in a case where the present example is adopted. A graph P3 in FIG. 9 corresponds to a case where the eccentric shaft is rotated in the state shown in FIG. 8(a), and a graph P4 corresponds to a case where the eccentric shaft is rotated in the state shown in FIG. 8(b). A graph P5 in FIG. 9 corresponds to a case where the weight 126 is positioned in the vicinity of a center of an area in which the male screw 112c is formed in the eccentric shaft main body 112.

THIRD EXAMPLE

Figure 10:
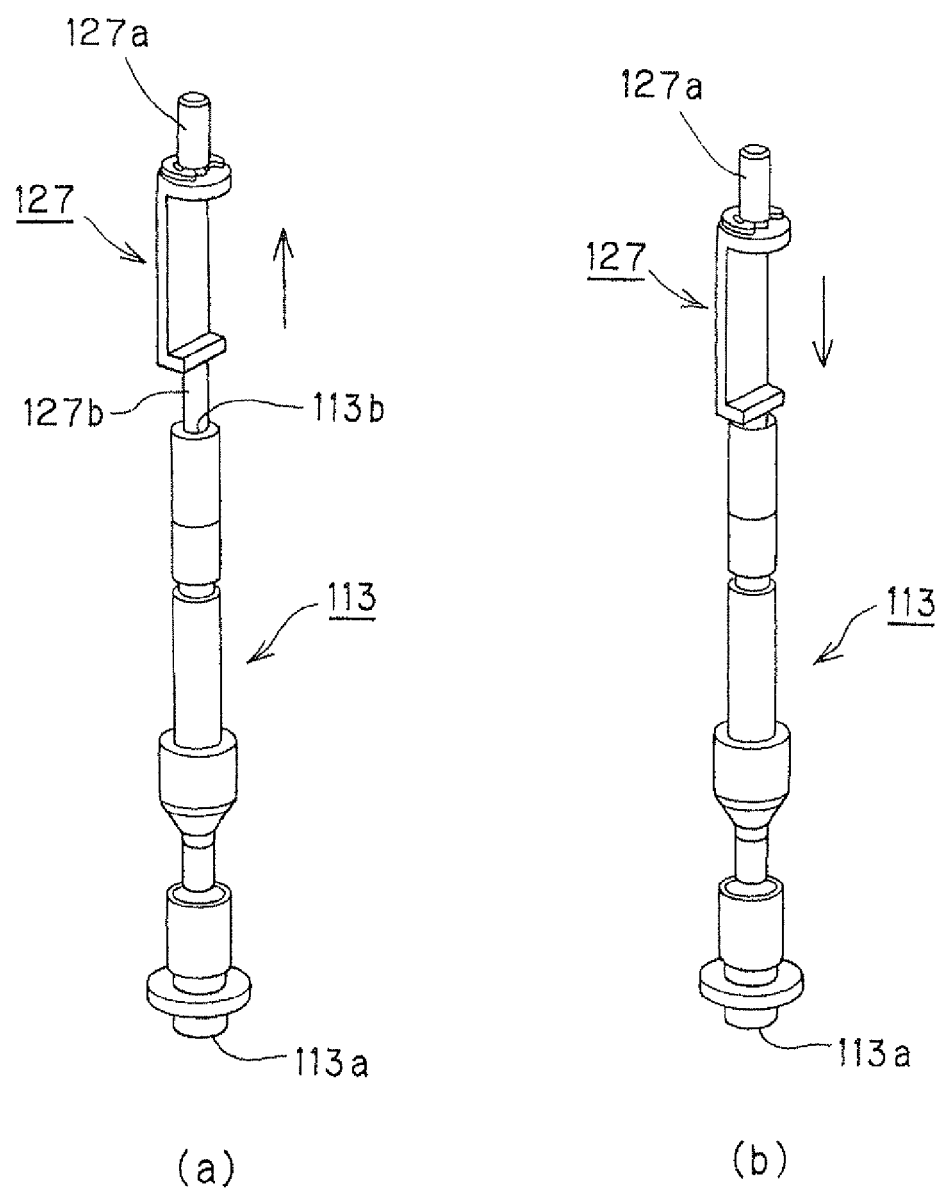
FIGS. 10(a) and 10(b) are perspective views of the eccentric shaft of the electric toothbrush according to a third example of the present invention.

With reference to FIGS. 10(a) and 10(b), the electric toothbrush according to a third example of the present invention will be described. The eccentric shaft according to the present example is a more specific example of the embodiment described with reference to FIGS. 4(a) and 4(b). FIGS. 10(a) and 10(b) are perspective views of the eccentric shaft of the electric toothbrush according to the third example of the present invention.

In an eccentric shaft main body 113 in the eccentric shaft according to the present example, a hole portion 113a into which the front end of the rotation shaft 23a of the motor 23 is fitted is provided in one end of the eccentric shaft main body, and an insertion hole 113b is provided in the other end. In a weight 127 in the eccentric shaft according to the present example, a shaft portion 127b to be inserted into the insertion hole 113b is provided in one end of the weight, and a shaft portion 127a supported by the bearing 31 of the stem 3 is provided in the other end. In the present example, the shaft portion 127b of the weight 127 can be inserted into and taken out from the insertion hole 113b of the eccentric shaft main body 113 with little insertion and take-out force. In order to rotate the weight 127 together with the eccentric shaft main body 113, sectional shapes of the shaft portion 127b and the insertion hole 113b which are perpendicular to the shaft are both formed into non-circular shapes (however, a circular part may be included partly).

With the above configuration, in a case of the eccentric shaft according to the present example, when the eccentric shaft is inclined so as to direct the weight 127 to face the lower side, the weight 127 is moved in the direction in which the weight is brought distant from the eccentric shaft main body 113 by a gravitational force, and when the eccentric shaft is inclined so as to direct the weight 127 to face the upper side, the weight 127 is moved in the direction in which the weight is brought close to the eccentric shaft main body 113 by the gravitational force. Therefore, in a case where the eccentric shaft according to the present example is adopted, the gravity center position of the eccentric shaft can be moved in the axial direction by a posture of the electric toothbrush, and hence the resonant frequency of the eccentric shaft can be changed.

FIG. 10(a) corresponds to the model of FIG. 4(b), and FIG. 10(b) corresponds to the model of FIG. 4(a).

FOURTH EXAMPLE

Figure 11:
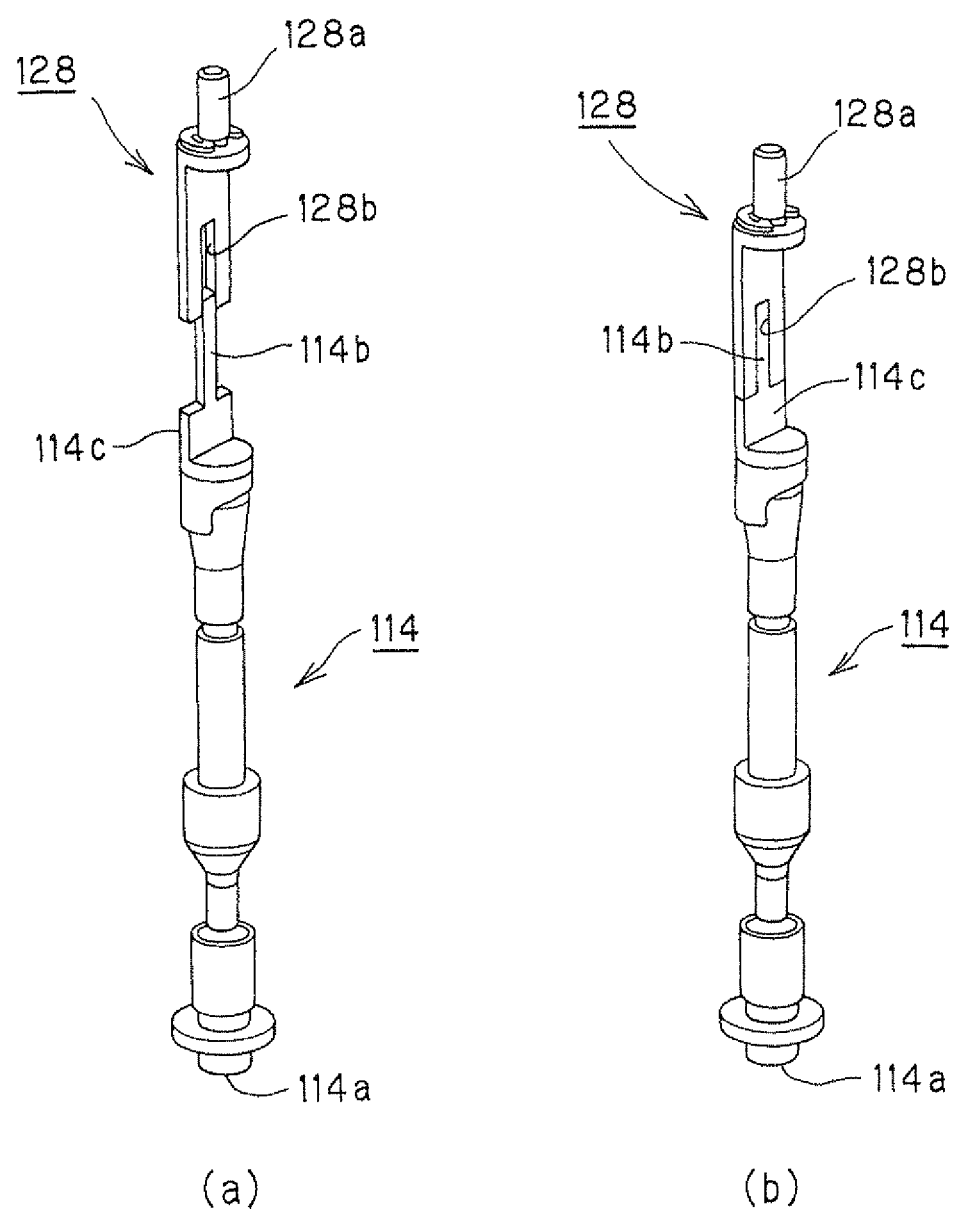
FIGS. 11(a) and 11(b) are perspective views of the eccentric shaft of the electric toothbrush according to a fourth example of the present invention.

With reference to FIGS. 11(a) and 11(b), the electric toothbrush according to a fourth example of the present invention will be described. The eccentric shaft according to the present example is a more specific example of the embodiment described with reference to FIGS. 4(a) and 4(b). FIGS. 11(a) and 11(b) are perspective views of the eccentric shaft of the electric toothbrush according to the fourth example of the present invention.

In an eccentric shaft main body 114 in the eccentric shaft according to the present example, a hole portion 114a into which the front end of the rotation shaft 23a of the motor 23 is fitted is provided in one end of the eccentric shaft main body, and a first weight 114c provided with a protruding portion 114b is fixed to the other end. In the present example, a second weight 128 is provided in line in the axial direction on the side of a distal end of the eccentric shaft main body 114. In the second weight 128, a slit portion 128b into which the protruding portion 114b is inserted is provided in one end of the second weight, and a shaft portion 128a supported by the bearing 31 of the stem 3 is provided in the other end. In the present example, the protruding portion 114b of the eccentric shaft main body 114 can be inserted into and taken out from the slit portion 128b of the second weight 128 with little insertion and take-out force.

With the above configuration, in a case of the eccentric shaft according to the present example, when the eccentric shaft is inclined so as to direct the second weight 128 to face the lower side, the second weight 128 is moved in the direction in which the second weight 128 is brought distant from the eccentric shaft main body 114 by the gravitational force, and when the eccentric shaft is inclined so as to direct the second weight 128 to face the upper side, the second weight 128 is moved in the direction in which the second weight 128 is brought close to the eccentric shaft main body 114 by the gravitational force. Therefore, in a case where the eccentric shaft according to the present example is adopted, the gravity center position of the eccentric shaft can be moved in the axial direction by the posture of the electric toothbrush, and hence the resonant frequency of the eccentric shaft can be changed. FIG. 11(a) corresponds to the model of FIG. 4(b), and FIG. 11(b) corresponds to the model of FIG. 4(a).

FIFTH EXAMPLE

With reference to FIGS. 12(a) and 12(b), the electric toothbrush according to a fifth example of the present invention will be described. FIGS. 12(a) and 12(b) are perspective views of the eccentric shaft of the electric toothbrush according to the fifth example of the present invention.

In an eccentric shaft main body 115 in the eccentric shaft according to the present example, a hole portion 115a into which the front end of the rotation shaft 23a of the motor 23 is fitted is provided in one end of the eccentric shaft main body, and a first weight 115b is fixed to the other end. A plurality of teeth 115c is provided in an end surface of the first weight 115b.

In the present example, a second weight 129 is provided in line in the axial direction on the side of a distal end of the eccentric shaft main body 115. In the second weight 129, a shaft portion 129a supported by the bearing 31 of the stem 3 is provided in a distal end of a weight main body portion 129b. A plurality of teeth 129c to be meshed with the plurality of teeth 115*c* provided in the first weight 115*b* is provided in the other end surface of the weight main body portion 129*b*, thereby forming a ratchet mechanism.

Figure 12:
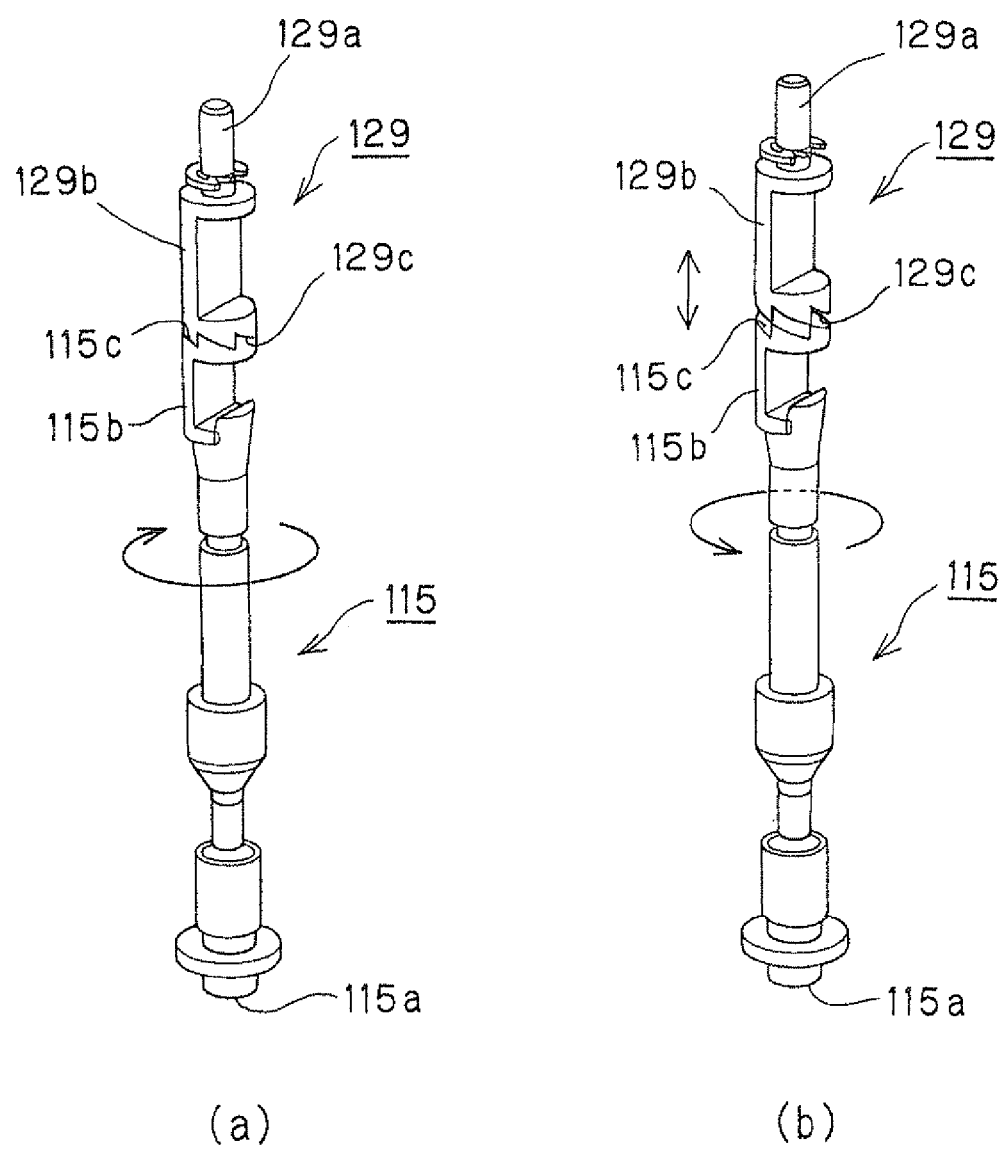
FIGS. 12(a) and 12(b) are perspective views of the eccentric shaft of the electric toothbrush according to a fifth example of the present invention.

With the above configuration, in a case of the eccentric shaft according to the present example, when the eccentric shaft main body 115 is rotated in the arrow direction shown in FIG. 12(*a*), the second weight 129 is not rotated relative to the eccentric shaft main body 115 but rotated together with the eccentric shaft main body 115.

When the eccentric shaft main body 115 is rotated in the opposite direction (the arrow direction shown in FIG. 12(*b*)), the second weight 129 is rotated relative to the first weight 115*b* fixed to the eccentric shaft main body 115. Therefore, in this case, the distance between the gravity center position of the eccentric shaft and the shaft center can be changed. In a case where the second weight 129 is rotated relative to the first weight 115*b*, the second weight 129 is also moved in the axial direction for getting over the teeth 115*c*, 129*c* respectively provided in the weights. Thus, the gravity center position of the eccentric shaft can be periodically moved in the axial direction.

SIXTH EXAMPLE

Figure 13:
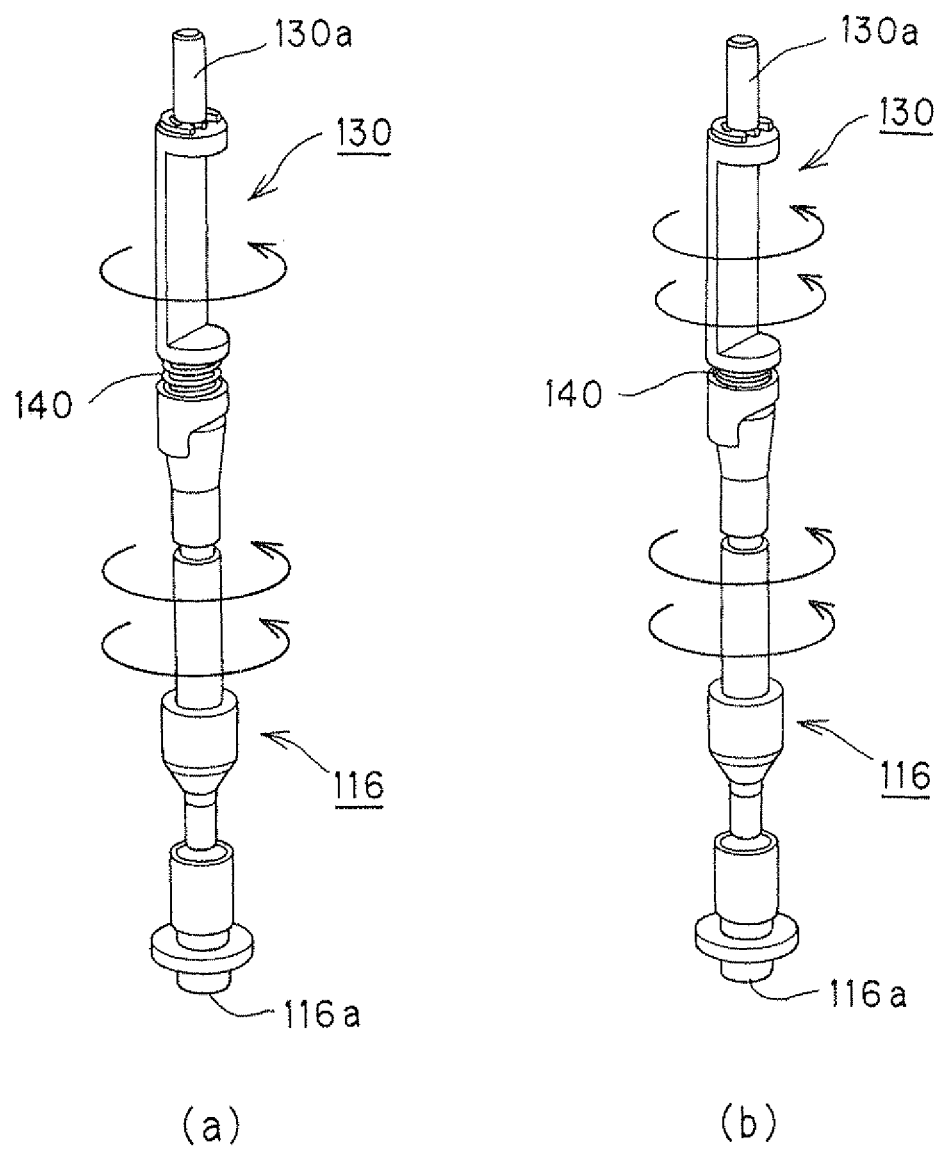
FIGS. 13(a) and 13(b) are perspective views of the eccentric shaft of the electric toothbrush according to a sixth example of the present invention.

With reference to FIGS. 13(*a*) and 13(*b*), the electric toothbrush according to a sixth example of the present invention will be described. FIGS. 13(*a*) and 13(*b*) are perspective views of the eccentric shaft of the electric toothbrush according to the sixth example of the present invention.

In an eccentric shaft main body 116 in the eccentric shaft according to the present example, a hole portion 116*a* into which the front end of the rotation shaft 23*a* of the motor 23 is fitted is provided in one end of the eccentric shaft main body. A weight 130 is provided in line in the axial direction on the side of a distal end of the eccentric shaft main body 116. A shaft portion 130*a* supported by the bearing 31 of the stem 3 is provided in a front end of the weight 130. In the present example, a coil spring 140 is provided between the eccentric shaft main body 116 and the weight 130. One end of the coil spring 140 is fixed to the eccentric shaft main body 116, and the other end is fixed to the weight 130.

With the above configuration, in a case of the eccentric shaft according to the present example, the weight 130 is moved by the gravitational force and extension and compression of the coil spring 140 in accordance with the posture of the electric toothbrush. Thus, the gravity center position of the eccentric shaft can be moved in the axial direction. The eccentric shaft main body 116 and the weight 130 are connected via the coil spring 140. Thus, at the time of start-up, the weight 130 is slowly rotated at the beginning, rotation speed is gradually increased, and the rotation speed becomes the same as rotation speed of the eccentric shaft main body 116 at the end. FIG. 13(*a*) shows a state immediately after the start-up, and FIG. 13(*b*) shows a state after sufficient time elapses and the rotation speed of the weight 130 becomes the same as the rotation speed of the eccentric shaft main body 116. In the figures, the number of arrows indicates a difference in the rotation speed (the more the arrows are, the faster the rotation speed is).

As described above, in a case of the present example, the gravity center of the eccentric shaft is hardly influenced by a weight of the weight 130 immediately after the start-up. As the rotation speed of the weight 130 becomes faster, the influence of the weight of the weight 130 gradually becomes larger. Thus, the gravity center of the eccentric shaft is gradually moved from a position of the shaft center to a position distant from the shaft center. Therefore, at the time of start-up, the vibration amplitude of the eccentric shaft is gradually increased. Thereby, in a case of brushing the teeth, the brush portion 41 can be prevented from radically vibrating immediately after the power supply is turned on, and feel of stimulation can be suppressed.

SEVENTH EXAMPLE

Figure 14:
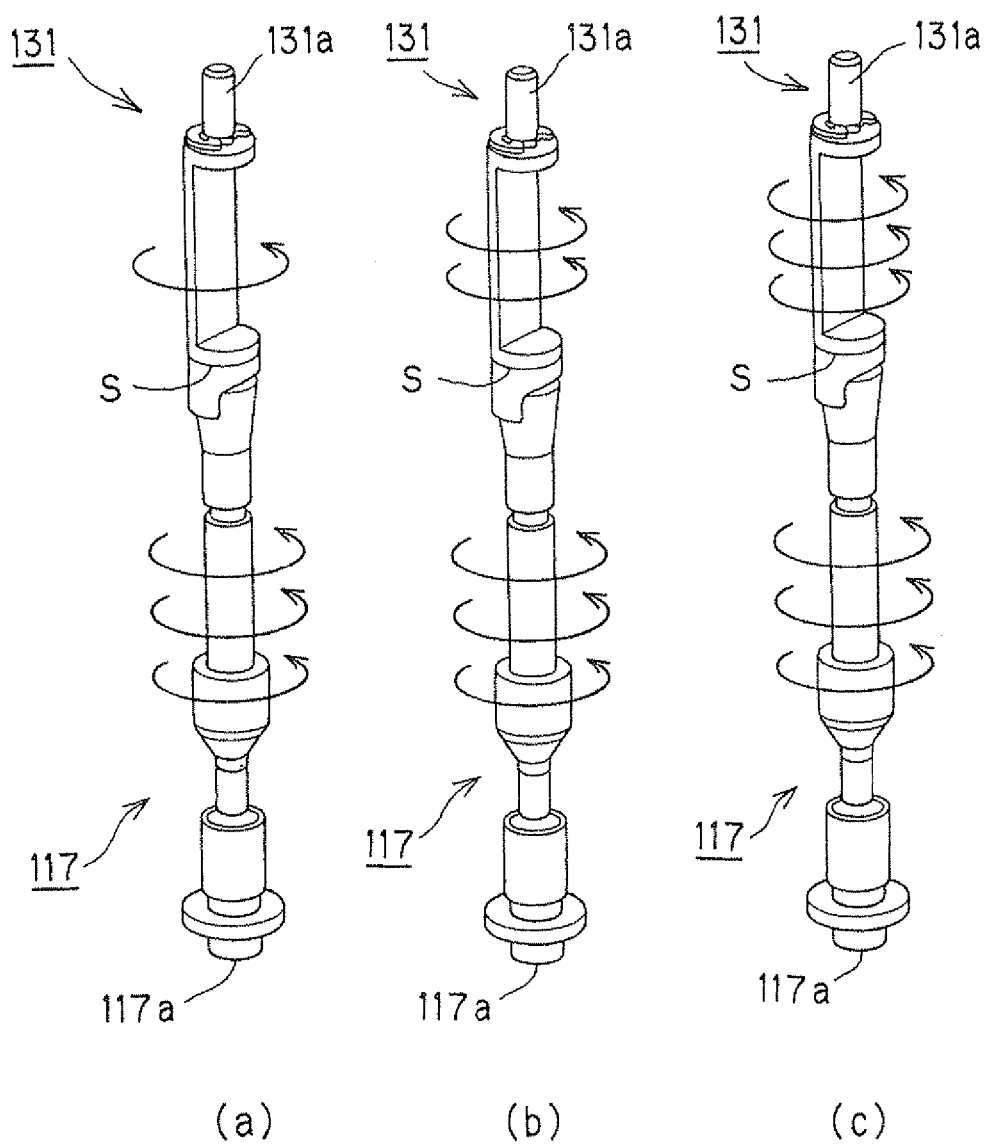
FIGS. 14(a) to 14(c) are perspective views of the eccentric shaft of the electric toothbrush according to a seventh example of the present invention.
Figure 15:
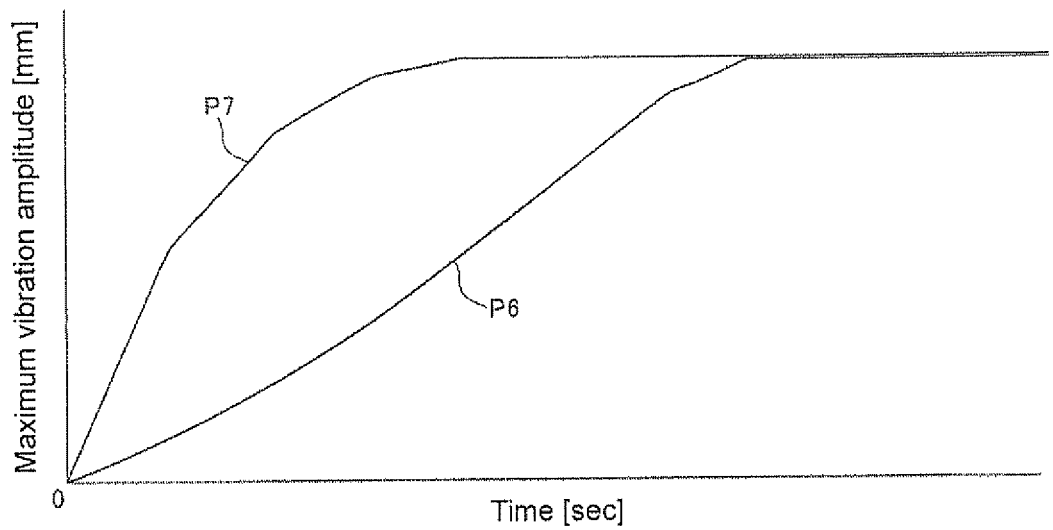
FIG. 15 is a graph showing a relationship between elapsed time at the time of start-up and maximum vibration amplitude in the electric toothbrush according to the seventh example of the present invention.

With reference to FIGS. 14(*a*) to 14(*c*) and FIG. 15, the electric toothbrush according to a seventh example of the present invention will be described. FIGS. 14(*a*) to 14(*c*) are perspective views of the eccentric shaft of the electric toothbrush according to the seventh example of the present invention. FIG. 15 is a graph showing a relationship between elapsed time at the time of start-up and maximum vibration amplitude in the electric toothbrush according to the seventh example of the present invention.

In an eccentric shaft main body 117 in the eccentric shaft according to the present example, a hole portion 117*a* into which the front end of the rotation shaft 23*a* of the motor 23 is fitted is provided in one end of the eccentric shaft main body. A weight 131 is provided in line in the axial direction on the side of a distal end of the eccentric shaft main body 117. A shaft portion 131*a* supported by the bearing 31 of the stem 3 is provided in a front end of the weight 131. In the present example, a fluid (such as oil and grease) is placed in a clearance S between the eccentric shaft main body 117 and the weight 131.

With the above configuration, in a case of the eccentric shaft according to the present example, when the eccentric shaft main body 117 is rotated, by the so-called principle of a fluid clutch, the weight 131 is slowly rotated at the beginning, rotation speed is gradually increased, and the rotation speed becomes the same as rotation speed of the eccentric shaft main body 117 at the end. FIG. 14(*a*) shows a state immediately after the start-up, FIG. 14(*b*) shows a state time elapses a little after the start-up, and FIG. 14(*c*) shows a state after sufficient time elapses and the rotation speed of the weight 131 becomes the same as the rotation speed of the eccentric shaft main body 117. In the figures, the number of arrows indicates a difference in the rotation speed (the more the arrows are, the faster the rotation speed is).

As described above, in a case of the present example, the gravity center of the eccentric shaft is hardly influenced by a weight of the weight 131 immediately after the start-up. As the rotation speed of the weight 131 becomes faster, the influence of the weight of the weight 131 gradually becomes larger. Thus, the gravity center of the eccentric shaft is gradually moved from a position of the shaft center to a position distant from the shaft center. Therefore, at the time of start-up, the vibration amplitude of the eccentric shaft is gradually increased. Thereby, in a case of brushing the teeth, the brush portion 41 can be prevented from radically vibrating immediately after the power supply is turned on, and the feel of stimulation can be suppressed. In FIG. 15, a graph P6 shows the elapsed time at the time of start-up and the maximum vibration amplitude in the eccentric shaft according to the present example. A graph P7 in the figure shows the elapsed time at the time of start-up and the maximum vibration amplitude in a case where the weight is fixed to the eccentric shaft (comparative example).

In the present example, the weight 131 and the eccentric shaft main body 117 are not fixed to each other. However, inside the electric toothbrush 1, the weight 131 and the eccentric shaft main body 117 are required to be formed so that center shafts are not shifted from each other. Two examples of configurations for realizing this will be described. Configurations described below can be applied to the relationship between the second weight 125 and the eccentric shaft main body 111 in the first example described above.

<<Utilizing Convexo-concave Fit>>

Figure 16:
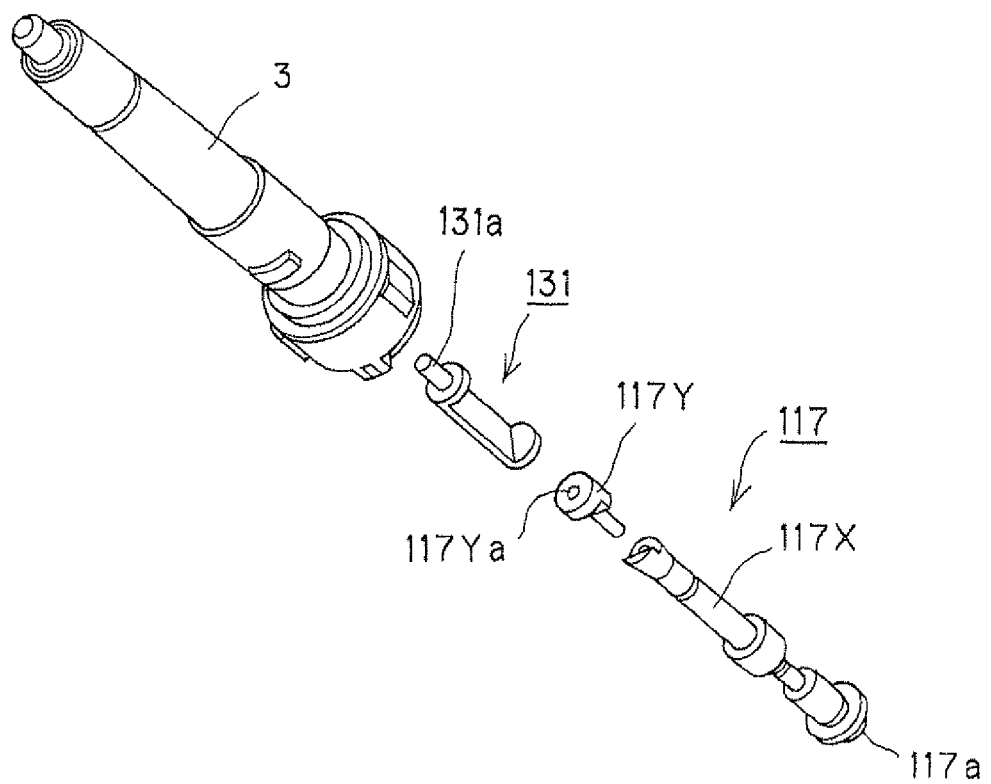
FIG. 16 is an exploded view of parts of the eccentric shaft and a stem in the electric toothbrush according to the seventh example of the present invention.
Figure 17:
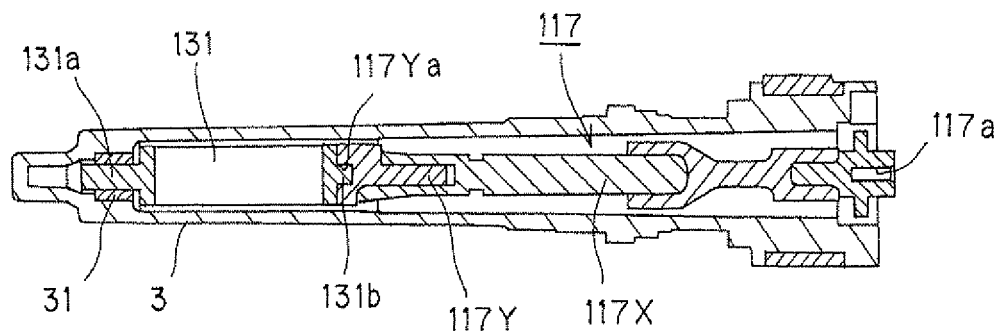
FIG. 17 is a schematic sectional view of the eccentric shaft and the stem in the electric toothbrush according to the seventh example of the present invention.

With reference to FIGS. 16 and 17, a configuration in which convexo-concave fit is utilized so that the center shafts of the weight 131 and the eccentric shaft main body 117 are not shifted from each other will be described. The eccentric shaft main body 117 is formed by a trunk 117X in which the hole portion 117a is provided in one end, and a metal component 117Y excellent in a wear characteristic to be fixed to a front end of this trunk 117X. The trunk 117X is made of resin or elastomer. A concave portion 117Ya is formed in a front end of the metal component 117Y. Meanwhile, a convex portion 131b to be fitted to the concave portion 117Ya of the metal component 117Y is provided in an end of the weight 131 on the opposite side of the shaft portion 131a.

With the above configuration, the center shafts can be prevented from being shifted from each other without fixing the weight 131 and the eccentric shaft main body 117.

<<Inner Wall Surface of Stem Functioning as Bearing>>

Figure 18:
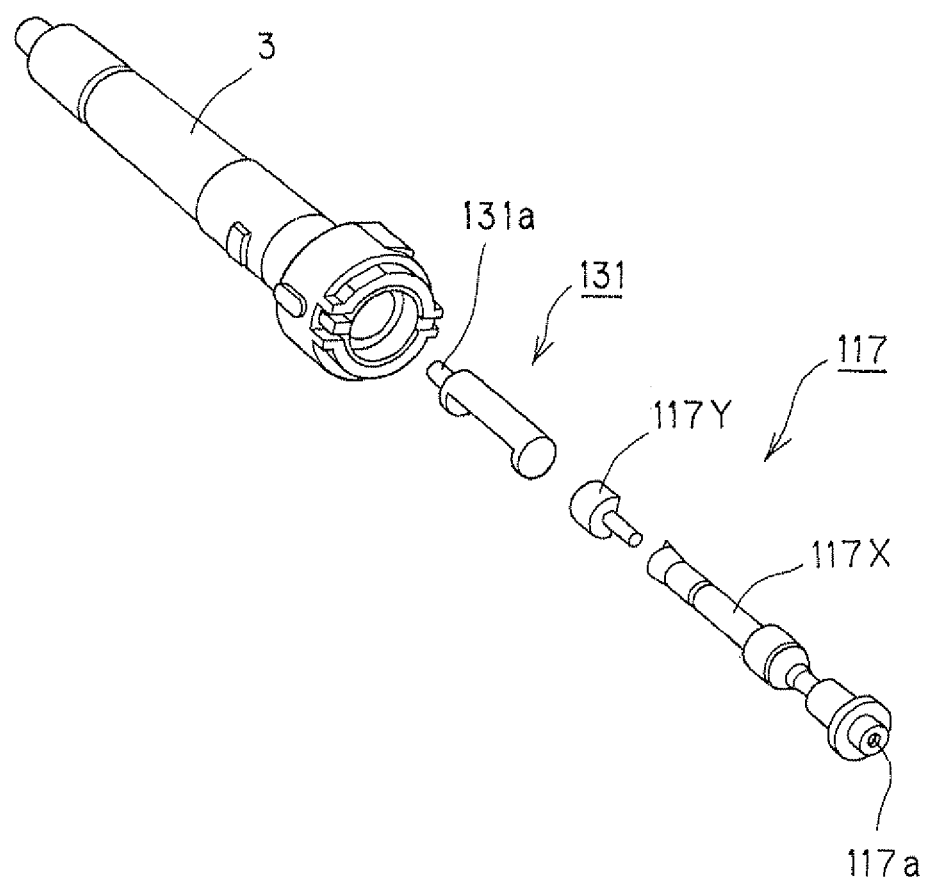
FIG. 18 is an exploded view of parts of the eccentric shaft and the stem in the electric toothbrush according to the seventh example of the present invention.
Figure 19:
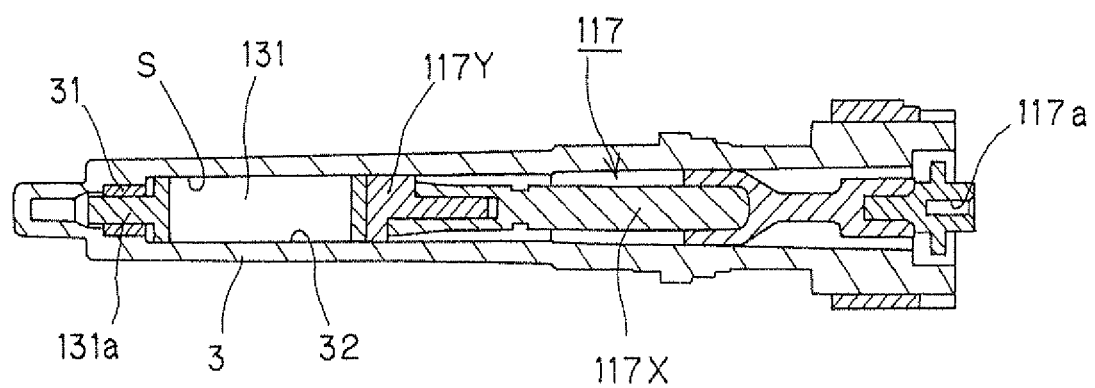
FIG. 19 is a schematic sectional view of the eccentric shaft and the stem in the electric toothbrush according to the seventh example of the present invention.

With reference to FIGS. 18 and 19, a configuration in which an inner wall surface 32 of the stem 3 functions as a bearing so that the center shafts of the weight 131 and the eccentric shaft main body 117 are not shifted from each other will be described. The eccentric shaft main body 117 is formed by the trunk 117X in which the hole portion 117a is provided in the one end, and the metal component 117Y excellent in the wear characteristic to be fixed to the front end of the trunk 117X. The trunk 117X is made of resin or elastomer. The front end of the metal component 117Y is formed into a plane. The end of the weight 131 on the opposite side of the shaft portion 131a is formed into a plane.

In this example, a clearance S between the inner wall surface 32 of the stem 3 and an outer circumferential surface of the metal component 117Y and between the inner wall surface 32 of the stem 3 and an outer circumferential surface of the weight 131 is set to be as small as possible. Thereby, the inner wall surface 32 of the stem 3 functions as a bearing for the metal component 117Y and the weight 131.

With the above configuration, the center shafts can be prevented from being shifted from each other without fixing the weight 131 and the eccentric shaft main body 117.

(Others)

In the above embodiment and the examples, the case where the end of the eccentric shaft on the opposite side of the end fixed to the rotation shaft 23a of the motor 23 is supported by the bearing 31 provided in the stem 3 is exemplified and described. In a case where such a configuration is adopted, as described in the above embodiment, the stem 3 is vibrated via the bearing 31, and the vibration is transmitted to the brush component 4. Since the bearing 31 is positioned in the vicinity of the brush portion 41, the vibration can be efficiently transmitted to the brush portion 41.

However, as the electric toothbrush in which the eccentric shaft is adopted, there is a type of electric toothbrush in which an eccentricity weight is arranged in the vicinity of the rotation shaft of the motor so that the end of the eccentric shaft on the opposite side of the end fixed to the rotation shaft of the motor is not supported by the bearing (the distal end of the eccentric shaft serves as a free end). The present invention can be also applied to such a type of electric toothbrush. That is, the above eccentric shaft may be applied to such a type of electric toothbrush.

The invention claimed is:

1. An electric toothbrush, comprising:
   a motor;
   a case which accommodates the motor;
   an eccentric shaft having a first end and a second end, the first end thereof fixed to a rotation shaft of the motor and the second end thereof held by the case, the eccentric shaft being able to rotate in a forward direction and a reverse direction by the motor;
   a brush component mounted on the case; and
   a gravity center horizontally shifting arrangement having a lower weight and an upper weight provided in the eccentric shaft and aligned along the rotation shaft so as to locate the lower weight closer to the motor than the upper weight, at least one of the upper weight and lower weight being configured to angularly rotate between a first engaged position and a second engaged position about the rotation shaft, whereby the gravity center in a radial direction of a center axis of the eccentric shaft is shifted to a first radial position spaced from and close to the center axis when the eccentric shaft is rotated in the forward direction to rotate the weight to the first engaged position, and the gravity center is shifted to a second radial position further away from the center axis than the first radial position when the eccentric shaft is rotated in the reverse direction to rotate the weight to the second engaged position.

2. The electric toothbrush according to claim 1, wherein the lower weight is firmly fixed to the eccentric shaft; and the upper weight is loosely mounted on the eccentric shaft, wherein the upper weight freely rotates about the shaft between the first engaged position accomplished by a first stopper and the second engaged position accomplished by a second stopper,
   whereby the upper weight is held in the first engaged position when the eccentric shaft is rotated in the forward direction and the upper weight is held in the second engaged position when the eccentric shaft is rotated in the reverse direction.

3. The electric toothbrush according to claim 1, wherein the gravity center horizontally shifting arrangement comprises:
   a ratchet gear arrangement provided at a joint between the upper weight and the lower weight.

* * * * *